United States Patent [19]

Baldus et al.

[11] Patent Number: 5,155,272
[45] Date of Patent: Oct. 13, 1992

[54] PROCESS FOR THE PRODUCTION OF HALOACYLAMIDES

[75] Inventors: Donald E. Baldus, Belleville, Ill.; Edward E. Debus, Chesterfield, Mo.

[73] Assignee: Monsanto Company, St. Louis, Mo.

[21] Appl. No.: 592,730

[22] Filed: Oct. 4, 1990

Related U.S. Application Data

[63] Continuation of Ser. No. 218,777, Jul. 14, 1988, abandoned, which is a continuation-in-part of Ser. No. 13,597, Feb. 11, 1987, abandoned, which is a continuation of Ser. No. 799,383, Nov. 18, 1985, abandoned, which is a continuation of Ser. No. 591,644, Mar. 20, 1984, abandoned, which is a continuation of Ser. No. 460,508, Jan. 24, 1983, abandoned, which is a continuation of Ser. No. 844,542, Oct. 26, 1977, abandoned, which is a continuation-in-part of Ser. No. 755,279, Dec. 29, 1976, abandoned.

[51] Int. Cl.$^5$ .......................................... C07C 231/12
[52] U.S. Cl. ............................................ 564/214; 558/414
[58] Field of Search ............... 564/85, 102, 209, 210, 564/211, 212, 214; 558/414

[56] References Cited

U.S. PATENT DOCUMENTS

| | | | |
|---|---|---|---|
| 2,863,752 | 12/1958 | Hamm et al. | 260/562 B |
| 3,442,945 | 5/1969 | Olin | 260/561 HL |
| 3,547,620 | 12/1970 | Olin | 71/118 |
| 3,574,746 | 4/1971 | Chupp | 260/562 HL |
| 3,637,847 | 1/1972 | Olin | 260/562 B |
| 3,875,228 | 4/1975 | Rathgeb et al. | 260/562 R |
| 3,876,700 | 4/1975 | Ross et al. | 260/562 B |
| 3,937,730 | 2/1976 | Vogel et al. | 260/562 B |
| 3,947,508 | 3/1976 | Correia et al. | 260/654 S |
| 3,952,056 | 4/1976 | Vogel et al. | 71/118 X |
| 4,070,179 | 1/1978 | Vogel et al. | 71/118 |
| 4,399,306 | 8/1983 | Donjan | 564/214 |
| 4,511,736 | 4/1985 | Migyorodi et al. | 564/214 |

FOREIGN PATENT DOCUMENTS

| | | |
|---|---|---|
| 816559 | 12/1974 | Belgium . |
| 18706 | 3/1978 | Israel . |
| 103351 | 6/1983 | Japan .................... 564/214 |

*Primary Examiner*—Carolyn Elonore
*Attorney, Agent, or Firm*—William I. Andress

[57] ABSTRACT

The disclosure herein concerns a new process for producing haloacylamides, particularly haloacelanilides typified by 2',6'-diethyl-N-(methoxymethyl)2-chloroacetanilide (common name alachlor), by the reaction of the appropriate haloacyl amides one of which substituents has a reactive halogen atom with the appropriate alcohol or thioalcohol.

18 Claims, No Drawings

PROCESS FOR THE PRODUCTION OF HALOACYLAMIDES

CROSS-REFERENCE TO RELATED APPLICATIONS

This application is a Continuation of Ser. No. 07/218,777, filed Jul. 14, 1988, which is a Continuation-in-part of Ser. No. 07/013,597 filed Feb. 11, 1987, which is a Continuation of Ser. No. 06/799,383 filed Nov. 18, 1985, which is a Continuation of Ser. No. 06/591,644 filed Mar. 20, 1984, which is a Continuation Ser. No. 06/460,508 filed Jan. 24, 1983 which is a Continuation of Ser. No. 05/844,542 filed Oct. 26, 1977, which is a Continuation-in-part of Ser. No. 05/755,279 filed Dec. 29, 1976, all abandoned.

BACKGROUND OF THE INVENTION

1. Field of the Invention

The invention herein relates to the field of chemical processes for the preparation of haloacylamides, particularly haloacetanilides, useful in the agronomic arts, e.g., as pesticides and plant growth regulators.

2. Description of the Prior Art

Haloacylamides and haloacetanilides of the type described herein have been prepared by a variety of means known to the prior art. In one prior art process, described in U.S. Pat. No. 2,863,752 (Re 26,961) N-substituted-2-haloacetanilides are prepared by reacting a primary or secondary amine with the acid chloride of haloacetic acid typically in the presence of caustic soda to neutralize the by-product hydrogen halide. A similar process is described in German OLS 1,903,198 wherein the intermediates and final products are characterized by the N-substituent loweralkoxyethyl wherein the ethyl radical may have one or two methyl groups attached thereto.

In yet another prior art process described in U.S. Pat. No. 3,574,746, N-substituted-N-cycloalkenyl-2-haloacetamides are prepared by the haloacetylation of the corresponding N-substituted-cycloalkylimine in the presence of an acid acceptor.

Still another prior art process for producing 2-haloacetanilides is described in U.S. Pat. Nos. 3,442,945 and 3,547,620 wherein the appropriate intermediate compound, an N-halomethyl-2-haloacetanilide, is reacted with the appropriate alcohol preferably in the presence of an acid binding agent. An analogous process is described in Canadian Patent No. 867,769 wherein fluoroacylamino-trichloromethyl-chloromethane is reacted with a thio compound of the formula Me-S-R where Me is H or alkali metal; when the thio compound is used in the free form it is expedient to use an acid-binding agent; when the thio compounds are used in the form of their salts, it is not necessary to add an acid binding agent.

The processes of each of the above '752, '945 and '620 patents are also described in U.S. Pat. No. 3,875,228 as useful in the preparation of 2-haloacetamides (also described as acylamines) exemplified by N-chloroacetyl-N-substituted (hydrogen, lower alkyl, alkoxymethyl, allyloxymethyl or methoxyethyl)-aminoindanes.

As relevant to the present invention involving the alcoholysis of the N-haloalkyl-N-substituted 2-haloacylamide or 2-haloacetanilide intermediate, the prior art (see, e.g., the above '945, '620 and '228 patents) describes the preparation of the 2-haloacetanilide intermediate by the haloacetylation of the appropriate phenylazomethine. See also U.S. Pat. No. 3,637,847.

In another process described in the Journal of the Chemical Society, Volume 1, pages 2087–88 (1974) by O. O. Orazi et al, N-halo-N-substituted amides and imides are methylenated at the nitrogen-halogen bond using diazomethane to produce the corresponding N-halomethyl-N-substituted-amide or imide followed by condensation with nucleophiles. One species of this process involves the reaction of N-chloro-N-methyl-2-chloroacetamide with diazomethane to produce the corresponding N-chloromethyl-N-methyl-2-chloroacetamide, which can then be reacted with a nucleophile.

In the above-mentioned '746 patent, Examples 57 and 54, respectively, disclose N-chloromethyl and N-bromomethyl-N-substituted-cycloalkenyl-2-haloacetamides which are representative of this class of compounds which can serve as intermediates in the process of the present invention. Still other known processes for producing some intermediates used in this invention involve the N-haloalkylation of the appropriate aniline followed by N-haloacylation. For example, N-2-chloroethyl or N-2-chloro-1-methylethyl 2-haloacetanilides may be prepared by reacting the corresponding aniline with 2-chloroethyl-p-toluene-sulfonate and 2-chloro-1-methylethyl-p-toluene-sulfonate, respectively, followed by chloroacetylation. Still another process for preparing the N-haloalkyl intermediate involves reacting the appropriate haloalkane, e.g., 2-chloro-2-bromoethane, with the appropriate aniline followed by chloroacetylation.

In the process for producing N-substituted-2-haloacetanilides by alcoholysis of the corresponding N-haloalkyl-2-haloacetanilide intermediate compound, hydrogen halide is generated as a by-product which adversely affects not only the yield of desired product, but also adversely affects the natural environment. Hence, as indicated in the above '945, '620 and '228 patents, it is necessary that this alcoholysis be conducted in the presence of an acid-binding agent. Examples of acid-binding agents which have been used in the prior art include inorganic and organic bases such as the alkali metal and alkaline earth metal hydroxides, and carbonates, e.g., sodium and potassium hydroxide, sodium carbonate, etc., tertiary amines, e.g., trimethyl- and triethylamines, pyridine and pyridine bases, ammonia, quaternary ammonium hydroxides and alcoholates; metal alcoholates, e.g., sodium and potassium methylates, ethylates, etc. Both the hydrogen halide and the acid-binding agent can promote adverse side reactions which are undesirable, hence, constitute a disadvantage in prior art processes.

A significant disadvantage commonly encountered in the above-mentioned prior art processes is that the acid-binding agent reacts with the by-product hydrogen halide to form insoluble precipitates which must be separated from the reaction mixture and disposed of. Separation of the desired product from waste by-products frequently requires and/or includes stripping of any solvent used, aqueous washing, steam stripping of hydrogen halide, dehydration, filtration and/or stabilization of product. Other purification procedures include fractional distillation at sub or super atmospheric pressure, solvent extraction, film distillation, recrystallization, etc. For example, it is disclosed in Example 4 of each of the above '945 and '620 patents that in the production of N-(butoxymethyl)-2'-t-butyl-6'-methyl-2- chloroacetanilide (common name "terbuchlor"), the acid-binding agent, i.e., triethylamine, forms a voluminous precipitate of fine needles of triethylamine hydrochloride which must be removed by aqueous washing, solvent stripping and filtration. The same problem is also described in the above-mentioned '746 patent (see Column 6, lines 18–33).

As another example, when ammonia is used as the acid-binding agent in the production of 2',6'-diethyl-N-(methoxymethyl)-2-chloroacetanilide (common name "alachlor" and active ingredient in the commercial herbicide LASSO®, registered trademark of Monsanto Company), ammonium chloride is formed as a solid by-product in large quantity and must be disposed of.

In some instances, during or after the alcoholysis of the N-haloalkyl intermediate, the bulk of the generated hydrogen halide by-product can be removed by conventional distillation. However, the hydrogen halide itself is a gaseous pollutant in the environment. Moreover, in some cases distillation of the reactant alcohol and by-product hydrogen halide results in the production of an alkyl halide and water and water is detrimental to yield of product. Further, a certain percentage of the hydrogen halide remains in the reaction mixture and must be removed by an acid-binding agent, thus forming solid waste products as mentioned earlier. For example, in prior work on the alachlor process by another worker in the laboratories of applicants' assignee herein, efforts were made to remove by-product HCl with excess methanol by conventional vacuum distillation. However, these efforts involved prolonged exposure, i.e., ~2 hours, of the N-chloromethyl intermediate and final product (alachlor) to the adverse action of HCl, water and other by-products and resulted in greatly diminished yields of alachlor. It was then concluded that for optimum yield an acid-binding agent should be used during or after the distillation stage, hence encountering the attendant disadvantages mentioned above.

In view of energy conservation and environmental considerations bearing on the disposal of process wastes it has become exceedingly crucial to find new processes which eliminate or minimize the adverse impact of all kinds of wastes, i.e., solids, liquids and/or gases from chemical processing. In some instances deleterious by-products can be reprocessed for recycling of component parts. In other situations, by-products may be purified or converted to other useful products. However, each of the foregoing treatments require additional capital investment and reprocessing costs and energy consumption. Accordingly, it is much more desirable to avoid the creation of environmentally adverse products as far as possible.

Still another problem in connection with known prior art processes for the production of 2-haloacetanilides is that they are batch processes with attendant disadvantages, particularly on a commercial scale.

Therefore, it is an object of this invention to provide an improved process for producing 2-haloacylamides or 2-haloacetanilides which overcomes disadvantages of prior art processes. In particular it is an object of this invention to provide the advantages of a process which requires no acid-binding agent and produces substantially no solid wastes thereby eliminating some raw material, equipment and separation costs and solid waste disposal problems inimical to the environment.

Still other objects of this invention relate to a process which is continuous, simple and inexpensive in operation, conserves energy, reduces environmental pollution and yet produces yields and purities as great or greater than prior art processes.

SUMMARY OF THE INVENTION

The present invention relates to a continuous process for the preparation of N,N-disubstituted-haloacylamides, particularly compounds of Formula I

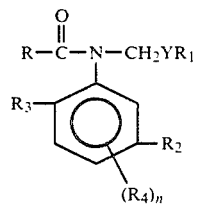

wherein
R is $C_{1-5}$ haloalkyl;
Y is oxygen or sulfur;
$R_1$ is $C_{1-10}$ alkyl, alkenyl, alkynyl, alkoxyalkyl, polyalkoxyalkyl, $C_{3-7}$ cycloalkyl, lower alkylcycloalkyl or cycloalkenyl, $C_{6-12}$ aryl, alkaryl or aralkyl, $C_{5-9}$ heterocyclic radicals containing 1–3 O, N and/or S atoms, or said $R_1$ members substituted with $C_{1-4}$ lower alkyl, haloalkyl, alkoxy, alkoxyalkyl or alkylthio, halogen, hydroxy, nitro or cyano;
$R_2$, $R_3$ and $R_4$ are independently hydrogen, halogen, $C_{1-6}$ alkyl, haloalkyl, alkoxy or alkoxyalkyl and
n is an integer from 0–4 inclusive, which comprises performing at least one sequence of reaction/separation operations comprising:

(A) reacting a compound of Formula II

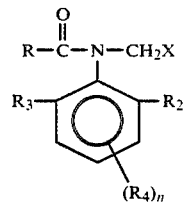

with a compound of Formula III $R_1YH$         (III)

wherein R, $R_1$–$R_4$, Y, and n are as defined above and X is halogen, and (B) directing an effluent stream of the reaction mixture from Step (A) to a separation zone from which is rapidly removed a complex of by-product HX with said compound of Formula III and a product stream comprising predominantly said compound of Formula I.

A preferred subgenus of compounds of particular interest which may be prepared by the process of this invention includes haloacetanilides of Formula I wherein R is monochloromethyl, $R_1$, $R_2$, $R_3$, and $R_4$ are $C_{1-6}$ alkyl, Y is oxygen and n is zero to 2, preferably zero.

In the most preferred embodiments, the process of this invention is used to prepare 2-chloroacetanilides according to Formula I wherein $R_1$, $R_2$ and $R_3$ are independently $C_{1-4}$ alkyl radicals, Y is oxygen and n is zero. Preferred alkyl radicals include methyl, ethyl, propyl, butyl and isomers of the latter two radicals. In a preferred specific application, the process of the invention is used to prepare alachlor by the reaction of 2',6'-diethyl-N-(chloromethyl)-2-chloroacetanilide and methanol as described in Example I below. Other preferred compounds prepared according to the process of this invention include 2'-ethyl-6'-methyl-N(ethoxymethyl)-2-chloroacetanilide (common name acetochlor) and 2',6'-diethyl-N-(butoxymethyl)-2-chloroacetanilide (common name butachlor).

In preferred embodiments, the above reaction/separation process sequence is repeated a plurality of times to assure complete conversion of said compound of Formula II to said compound of Formula I. In the most preferred embodiment the process is efficiently carried out in two stages or reaction/separation sequences which comprise:

(A) reacting in a first reaction zone a compound of Formula II with a compound of Formula III;

(B) directing an effluent stream of the reaction mixture of Step (A) to a first separation zone from which is rapidly removed most of by-product HX as a complex with said compound of Formula III and a product stream comprising predominantly a compound of Formula I and unreacted compound of Formula II;

(C) directing said product stream from said first separation zone to a second reaction zone into which is also introduced an additional quantity of said compound of Formula III to react with said unreacted compound of Formula II;

(D) directing an effluent stream of the reaction mixture of Step (C) to a second separation zone from which is rapidly removed substantially all of the remaining by-product HX as a complex with said compound of Formula III and a product stream comprised of said compound of Formula I and trace impurities.

Significant features of the process of this invention include: (1) the elimination of an added base as used in the prior art as an acid-binding agent for liberated hydrogen halide; and concomitantly (2) elimination of recovery systems for the neutralization by-product of (1) hence, elimination from the environment of the by-product itself and (3) initiation in the product separation zone of separation of by-product hydrogen halide as a complex with the compound of Formula III without delay upon reaching equilibration of the reaction mixture; preferably, this separation will occur within 0.5-5.0 min. after equilibration and will occur more rapidly with certain equipment, e.g., a flash evaporator immediately, i.e., within a few seconds, than other equipment, e.g., a rotary evaporator, which occurs rapidly and may require up to five minutes.

In preferred embodiments of the invention, the molar ratio of the compound of Formula III relative to the compound of Formula II in Step A is greater than 1:1 and usually within the range of about 2-100:1 and, in the case of the alachlor, acetochlor and butachlor processes, within the range of about 2-10:1 and preferably of 4-5:1.

The reaction temperatures in Step (A) will depend upon the particular reactants and/or solvents or diluents involved. In general, these temperatures will be temperatures at which mixtures of the alcohols of Formula III and/or solvents or diluents form complexes, e.g., azeotropic or modified forms of azeotropic mixtures, with by-product hydrogen halide without significant degradation of the reactant compound of Formula II or desired product of Formula I due to reaction with hydrogen halide. In general, a temperature within the range of from about $-25°$ to 125° C. or higher depending upon the melting/boiling points of the reactants is used.

In the single-stage operation embodiment of the process of this invention, under optimum conditions the desired 2-haloacetanilide product may be obtained in yields approximating, but somewhat less than, theoretical yield and a high degree of purity.

In those embodiments of the invention involving a plurality of reaction/separation sequences, or stages, the hydrogen halide concentration is further reduced in successive reaction zones, hence the respective reaction temperatures are generally somewhat elevated over the temperatures used in Step (A) in order to drive the reaction of the unreacted compound of Formula II to completion with additional alcohol. Accordingly, temperatures in the second and any subsequent reaction zone are generally within the range of from about $-25°$ to 175° C. or higher if necessary.

Suitably the temperatures and pressures within the separation zone(s) are, respectively, within the ranges of from about 50° C. to 175° C. and 1.0 to 300 mm Hg absolute, depending upon the boiling point of the particular compound of Formula III.

DETAILED DESCRIPTION OF THE INVENTION

EXAMPLE 1

This example describes the use of the process of this invention in the preparation of alachlor. This process is efficiently carried out in a reaction/separation sequence of two stages as follows:

Stage 1. Molten (45°-55° C.) 2',6'-diethyl-N-chloromethyl-2-chloroacetanilide is fed to an in-line mixer at a rate of 102.8 lbs/hr (46.67 kg/hr) and mixed with substantially anhydrous methanol which is fed to said mixer at a rate of 60.0 lbs/hr (27.24 kg/hr). The mixture is pumped through a thermostatted pipe reactor maintained at 40°-45° C. of sufficient length of give a residence time of at least thirty (30) minutes. The reaction produces a yield of ~92% 2',6'-diethyl-N-(methoxymethyl)-2-chloroacetanilide (alachlor) and hydrogen chloride based on the N-chloromethyl intermediate. The generated HCl is dissolved in excess methanol. The reactor effluent is directed to a falling film evaporator operated at 100° C. and 30 mm Hg absolute. A $CH_3OH/HCl$ complex is removed and fed to a methanol recovery system.

Stage 2. The product stream from the evaporator in Stage 1 comprising predominantly alachlor and unreacted 2',6'-diethyl-N-(chloromethyl)-2-chloroacetanilide is fed to a second in-line mixer into which is also fed an additional quantity of methanol at a rate of 60 lbs/hr (27.24 kg/hr). The mixture is then fed to a second reaction zone also comprising a thermostatted pipe reactor maintained at 60°-65° C. and of sufficient length to give a residence time of thirty (30) minutes. The effluent from this reactor is fed to a second falling film evaporator, operated at 100° C. and 30 mm Hg absolute, from which is removed a complex of methanol and substantially all of the remaining HCl. The methanol/HCl complex from this second stage evaporator is mixed with the methanol/HCl complex from the evaporator in Stage 1 and fed to a methanol recovery system from which anhydrous methanol is recovered and recycled to any preceding reaction zone. The physical nature of said complex is not clearly known; it is neither a simple mixture of the component alcohol and hydrogen halide nor a classic azeotropic mixture of those components, but may be some modified form of an azeotropic mixture. For lack of a clear understanding at its precise nature, the ROH/HX mixture is referred to as a "complex".

The product stream from the evaporator in Stage 2 comprises alachlor in essentially quantitative yield and greater than 95% purity together with minor amounts of impurities. This alachlor can be used effectively as a herbicide as produced.

As will be apparent from the foregoing example, the reaction/separation process sequence of Stage 1 by itself produces alachlor of high yield. Hence, under optimum conditions of reactant purities and concentrations, temperatures, residence times in the reactor and separation zones, etc., at least one reaction/separation process sequence corresponding to said Stage 1 operation would suffice to produce a commercial grade of alachlor or other compounds within the scope of the above Formula I.

EXAMPLE 2

This example describes the preparation of 2-chloro-2',6'-diethyl-N-(ethoxymethyl) acetanilide.

About 5.5 g (0.02 mole) of 2-chloro-2',6'-diethyl-N-(chloromethyl) acetanilide was dissolved in 25 ml of ethanol and allowed to stand in a 45° C. bath for 30 minutes. Excess ethanol was removed rapidly on a rotary vacuum evaporator at 50° C. and 10 mm Hg. Twenty-five (25) ml of fresh ethanol was added to the residual oil and the mixture held at 65° C. for 30 minutes. Again excess ethanol was removed using a rotary evaporator. About 5.80 g of a pale amber oil was obtained which assayed (by gas chromatography) 92.8% of the desired product and 1.7% 2-chloro-2',6'-diethylacetanilide (by-product). Yield of product was 94.5%.

EXAMPLE 3

Following the same procedure, operating conditions and quantities of reactants described in Example 2, but substituting isopropanol for ethanol, 5.92 gms of product, a light amber oil assaying 90.2% 2',6'-diethyl-N-(isopropoxymethyl)-2-chloroacetanilide (89.4% yield) and 1.8% of the secondary amide by-product, 2',6'-diethyl-2-chloroacetanilide was obtained.

EXAMPLE 4

Following the same procedure described in Examples 2 and 3, but substituting 1-propanol as the reactant alcohol, 5.66 gms of lemon-yellow oil was recovered with assayed 92.8% (87.9% yield) of 2',6'-diethyl-N-(n-propoxymethyl)-2-chloroacetanilide and 1.2% of the corresponding secondary amide by-product.

EXAMPLE 5

The same procedure described in Examples 2-4 was used in this example, but using isobutanol as the reactant alcohol, 6.20 gm of an oil product was recovered which assayed 96.4% (97% yield) of 2',6'-diethyl-N-(isobutoxymethyl) acetanilide and 3% of the corresponding secondary amide by-product.

EXAMPLE 6

Repeating the process of Examples 2-5, but using 2-chloroethanol as reactant alcohol, 6.96 gms of light-amber oil was recovered which assayed 86.0% (94.10% yield) of 2',6'-diethyl-N-(chloroethoxymethyl)-2-chloroacetanilide.

EXAMPLE 7

Following the same procedure described in Examples 2-6, but substituting n-butanol as the reactant alcohol, 6.18 gms of pale lemon-yellow oil was recovered which assayed 98.8% (99% yield) of 2',6'-diethyl-N-(n-butoxymethyl)-2-chloroacetanilide (i.e., butachlor) and 1% of the corresponding secondary amide by-product.

In the above examples, NMR analysis indicated that the respective products were consistent with chemical structure thereof.

EXAMPLE 8

Preparation of 2'-Methyl 6'-t-Butyl-(N-Methoxymethyl) 2-Bromoacetanilide

To 15.08 g (0.040 mole) 2'-methyl 6'-t-butyl (N-bromomethyl)-2-bromoacetanilide was added 25.0 g anhydrous methanol. The mixture was warmed to 45° C. and allowed to stand 30 minutes. Excess alcohol and HBr was removed on a rotary evaporator at 45° C./10 mm Hg. The oily residue was treated twice more with 25.0 g portions of anhydrous methanol in a similar fashion. After the final stripping, 13.0 g of clear, amber oil ($n^{26}_D$ 1.5470) was obtained, assaying 97.0% 2'-methyl 6'-t-butyl-(N-methoxymethyl) 2-bromoacetanilide by glc. The yield is 96.0%. NMR is consistent with structure and identical to product obtained when triethylamine is used as HBr scavenger.

EXAMPLE 9

Preparation of 2',6'-Dimethyl-(N-Isopropoxymethyl) 2-Chloroacetanilide

About 12.3 g (0.050 mole) of 2',6'-dimethyl (N-chloromethyl) 2-chloroacetanilide was dissolved in 30.0 g anhydrous isopropanol. The reaction mixture was warmed to 45°-50° C. for 30 minutes and excess alcohol and HCl stripped off using a rotary evaporator at 60° C./10 mm Hg. The residue was treated a second time with 30.0 g fresh isopropanol at 45° C. for 30 minutes. After stripping excess alcohol, 13.27 g of clear, pale lemon yellow oil ($n^{26}_D$ 1.5245) was obtained, assaying 93.9% by glc. The yield was 92.5%. NMR is consistent with structure and identical to product produced by alternate methods.

EXAMPLE 10

Preparation of 2-Chloro 2',6'-Diethyl-N-[(2-Methoxy-ethoxy)methyl)] acetanilide

To 13.71 g (0.050 mole) of 2',6'-diethyl-(N-chloromethyl) 2-chloroacetanilide was added 38.0 g of methyl cellosolve and allowed to stand at room temperature for 30 minutes. Excess alcohol and HCl was removed by rotary evaporator at 65° C./0.5 mm Hg. To the residual oil was added 38.0 g fresh methyl cellosolve and held at 45° C. for 30 minutes. Excess alcohol and HCl was removed, as before, to give 15.46 g of pale lemon yellow oil. Yield is 98.5%. Oil was taken up in n-hexane and recrystallized to give a white crystalline solid, MP 31.5-32.5° C.

EXAMPLE 11

Preparation of 2'-Ethyl, 6'-Methyl-(N-Ethoxymethyl)-2-Chloroacetanilide

To 10.4 g (0.04 mole) 2'-ethyl, 6'-methyl (N-chloromethyl)-2-chloroacetanilide was added 30.0 g ethanol and warmed to 45° C. for 15-20 minutes. Excess alcohol and HCl was removed under vacuum on a rotary evaporator. The residual oil was treated with 30.0 g fresh ethanol at 45° C. for 15 minutes and excess ethanol and HCl removed. After a third treatment, the residual oil weighed 10.73 g and assayed 96.4% by glc. The yield was 96.0%. Refractive index, $N^{25}_D$ 1.5236. NMR was consistent with structure and identical to product obtained when an acid scavenger was used.

EXAMPLE 12

Preparation of 2',6'-Diethyl-(N-Methoxymethyl) 2,2-Dichloroacetanilide

To 15.43 g (0.050 mole) of 2',6'-diethyl (N-chloromethyl) 2,2-dichloroacetanilide was added 32.0 g of anhydrous methanol. The reaction mixture was allowed to stand at 45° C. for 30 minutes and then alcohol/HCl was removed in vacuo on a rotary evaporator. The oily residue was treated two more times in the same manner and after stripping excess alcohol and HCl, 15.15 g of clear, pale lemon yellow oil ($n^{26}_D$ 26 1.5330) was obtained, assaying 98.3% by glc. The yield was 97.9%. NMR is consistent with structure and identical to product prepared using base as a HCl scavenger.

EXAMPLE 13

Preparation of 2'-Methyl, 6'-t-Butyl-(N-Allyloxy-methyl) 2-Chloroacetanilide

To 14.5 g (0.05 mole) 2'-methyl, 6'-t-butyl-(N-chloromethyl) 2-chloroacetanilide was added 29.0 g allyl alcohol and warmed to 45° C. for 15 minutes. Excess alcohol and HCl was removed under vacuum on a rotary evaporator and replaced with 29.0 g fresh allyl alcohol. The mixture was again held at 45° C. for 15 minutes. After stripping the excess alcohol and HCl, the sequence was repeated a third time. After the third stripping, 14.45 g (93.4% yield) of light amber oil $n^{26}_D$ 1.5338, was obtained. NMR was consistent with structure.

EXAMPLE 14

Preparation of 2'-Ethyl, 6'-Methyl-(N-Tetrahydrofurfuryloxymethyl) 2-Chloroacetanilide About 10.4 g (0.040 mole) of 2'-ethyl, 6'-methyl (N-chloromethyl) 2-chloroacetanilide was dissolved in 40.8 g (0.40 mole) tetrahydrofurfurylalcohol and allowed to stand overnight at room temperature. Excess alcohol and HCl was removed on a rotary evaporator at 65-70° C./0.4 mm Hg. A second portion of 40 g fresh alcohol was added to the residue and warmed to 45° C. for 30 minutes. Remove excess alcohol and HCl as before. Residue (13.0 g, 99.7% yield) is a light yellow oil, $n^{25}_D$ 1.5327. Proton NMR is consistent with structure.

EXAMPLE 15

Preparation of Acetamide, Alph-Chloro-N-(2,6 Dimethyl-1-Cyclohexen-1-yl)-N-(Methoxymethyl)

About 5.90 g (23.5 millimole) of 2',6'-dimethyl cyclohexen-1-yl-N-(chloromethyl) 2-chloroacetanilide was dissolved in 28.3 g of anhydrous methanol and allowed to stand at room temperature for 30 minutes. Excess methanol and HCl was removed under vacuum on a rotary evaporator. The above sequence was repeated twice more and after the final removal of methanol and HCl, 5.50 g (94.9%) of pale lemon yellow oil $n^{26}_D$ 1.5050) was obtained, Proton NMR is consistent with structure.

EXAMPLE 16

Preparation of 2'-Methyl, 6'-Methoxy-(N-Isopropoxymethyl) 2-Chloroacetanilide

To 3.30 g (12.6 millimoles) of 2'-methyl, 6'-methoxy-(N-chloromethyl) 2-chloroacetanilide was added 5.0 g (0.25 mole) anhydrous isopropanol and warmed to 45° C. for 30 minutes. Excess alcohol and HCl was removed under vacuum on a rotary evaporator and replaced with 15.0 g fresh isopropanol. The mixture was warmed to 45° C. and after 30 minutes, excess alcohol and HCl was removed to give 3.10 g of light amber oil, $n^{26}_D$ 1.5225. NMR is consistent with structure. The yield was 100%.

EXAMPLE 17

Preparation of 2',4',6'-Triethyl-(N-Methoxymethyl) 2-Chloroacetanilide

To 22.5 g (0.074 mole) of 2-chloro-2',4',6'-triethyl N-(chloromethyl) acetanilide in 30 ml of chlorobenzene is added 25 ml (20 g) of anhydrous methanol and allowed to stand at room temperature for 30 minutes. Excess methanol, HCl and some chlorobenzene was removed under vacuum on a rotary evaporator and a second 20 g portion of fresh methanol added to the residual oil. Again the mixture was allowed to stand at room temperature for 30 minutes. Methanol and HCl was stripped off again on a rotary evaporator and the sequence was repeated a third time. After the third stripping, 21.0 g of lemon yellow oil $n^{26}_D$ 1.5243) was obtained which assayed 97.7% 2',4',6' triethyl-(N-methoxymethyl) 2-chloroacetanilide, 1.0% 2',4',6' triethyl-2-chloroacetanilide (by-product) and 0.7% 2',4',640 triethyl-2,2-dichloroacetanilide (by-product). NMR is consistent with structure. The yield was 93.1%.

EXAMPLE 18

Preparation of 2',6'-Dimethyl-(N-Cyclohexyloxymethyl) 2-Chlororacetanilide

To 12.3 g (0.050 mole) of 2',6'-dimethyl (N-chloromethyl) 2-chloroacetanilide was added 50.0 g anhydrous cyclohexanol and the solution allowed to stand at room temperature overnight. Excess alcohol and HCl was stripped on a rotary evaporator at 65° C./1 mm Hg. Fresh cyclohexanol (50.0 g) was added to the residue and the solution warmed at 45° C. for 30 minutes. Excess alcohol and HCl was stripped off at 65° C./0.5 mm Hg to yield 15.45 g (99.7% yield) pale lemon yellow oil. Oil crystallized from cold hexane gives whole crystalline solid, melting point 46°-7° C. NMR is consistent with structure.

EXAMPLE 19

Preparation of 2'-Methyl, 6'-t-Butyl-(N-Cyclopropylmethoxymethyl) 2-Chloroacetanilide About 4.77 g of 2'-methyl, 6'-t-butyl (N-chloromethyl) 2-chloroacetanilide (0.016 mole) was dissolved in 9.60 g (0.132 mole) of cyclopropylcarbinol. The solution was allowed to stand one hour at room temperature and then excess alcohol and HCl was removed on a rotary evaporator at 55° C./1 mm Hg. About 9.6 g fresh cyclopropyl carbinol was added to the residual oil and the solution warmed to 45° C. for 20 minutes. Excess alcohol and HCl was again removed under vacuum as before to give a light amber, clear oil, $n^{26}_D$ 1.5280, weighing 5.28 g (98.9% yield).

EXAMPLE 20

Preparation of
2',6'-Dimethyl-N-(2-Methoxy-1-Methylethoxymethyl)
2-Chloroacetanilide About 12.3 g (0.050 mole) of 2',6'-dimethyl-N-(chloromethyl) 2-chloroacetanilide dissolved in twenty (20) ml of ethylene dichloride was added to 22.5 g (0.25 mole) of 2-methoxy-1-methyl ethanol. The solution was allowed to stand one hour at room temperature. Excess alcohol and HCl was removed under vacuum on a rotary evaporator. The residual oil was treated with an additional 22.5 g fresh alcohol for 30 minutes at 60° C. Excess alcohol and HCl was removed as before at 65° C./1 mm Hg. The light yellow oily residue weighed 14.86 g (99.1% yield). Refractive index of the oil, $n^{26}_D$ 1.5263. Proton NMR was consistent with structure.

EXAMPLE 21

Preparation of 2'-Methyl,
6'-Methoxy-N-(2-Methoxy-1-Methylethoxymethyl)
2-Chloroacetanilide About 4.60 g (0.017 mole) of 2' methyl-6'-methoxy-N-chloromethyl 2-chloroacetanilide dissolved in 15.8 g of 2-methoxy-1-methyl ethanol ("propanol") was warmed to 45° C. for 15 minutes. Excess alcohol and HCl was removed on a rotary evaporator at 55° C./1 mm Hg. The residue was treated again with 15.8 g of propanol for 15 minutes at 45° C. and excess alcohol and HCl removed as before. This sequence was repeated still a third time at 65° C. for 15 minutes and after final alcohol and HCl removal, 4.54 g (87.6%) of amber oil with refractive index, $n^{26}_D$ 1.5165, was obtained. Proton NMR was consistent with structure.

In further elaboration of the advantages provided by the present invention and the unobvious nature thereof, the following discussion is presented.

The reaction between compounds like those identified by Formula II and Formula III above is a reversible second-order reaction. Equation 1 below, exemplified by the reaction in Example 1, illustrates the reaction:

material (a) thus producing more product (c) and hydrogen halide by-product (d).

Another way to shift the equilibrium of Equation (1) to the right is to remove the hydrogen halide (d), which can be done by adding an acid-binder, e.g., tertiary amines such as triethylamine, as in U.S. Pat. Nos. 3,547,620, 3,442,945 and Canadian Patent No. 867,769 mentioned above. However, the use of acid-binding materials introduces other disadvantages as described earlier.

The foregoing Canadian '769 patent suggests that when the thio compound starting material is in the form of an alkali metal salt the acid-binding material is unnecessary; the apparent reason for this is that said salts themselves provide the basic medium, favorable to the particular reaction described in that patent. In contrast, when the starting thio compound is used in the free form, it is necessary to use an acid-binder to bind the hydrogen chloride by-product.

Although the process disclosed in the above '620 and '945 patents is described as being preferably conducted in the presence of an acid-binding agent (as exemplified in all of the specific working embodiments), an inference arises that the same process may be performed without the addition of an acid-binder. However, as mentioned earlier (in section entitled "Description of the Prior Art"), efforts to perform the process disclosed in the '945 and '620 patents to obtain the preferred product alachlor without an acid-binding agent to remove by-product hydrogen halide resulted in greatly diminished yields and quality of alachlor.

In practicing the present invention, no solvent is required, however, in many cases a solvent or diluent may be used to moderate the reaction and/or aid in the solution, dispersion and/or recovery of reactants, by-products and products. Suitable solvents or diluents include those which are inert under the required conditions of reaction, such as petroleum ether, CCl$_4$, aliphatic and aromatic hydrocarbons, e.g., hexane, benzene, toluene, xylenes, etc., and halogenated hydrocarbons, e.g., monochlorobenzene.

An advantage of the process according to this invention is that the reactant of Formula III may be readily separated from its complex with by-product hydrogen halide, purified and recycled to one or more reaction stages of the process. In like manner, the hydrogen halide itself may be readily recovered for use in many useful commercial operations, e.g., pickling of metals, oxychlorinations, electrolysis to elemental chlorine and hydrogen, etc., or otherwise disposed of without detriment to the environment.

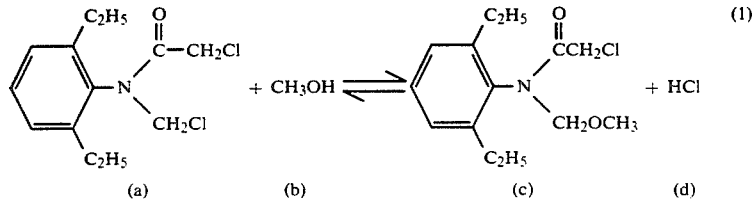

Because the reaction is reversible, an equilibrium condition is established; this equilibrium is affected by and directly related to various factors, e.g., alcohol concentration and/or by-product hydrogen halide concentration. For example, in Equation (1) as alcohol (b) concentration, hence reactants ratio, (b):(a), increases (to a given practical maximum) the equation is shifted to the right because of additional conversion of starting In one suitable raw material recovery/recycle system, exemplified with respect to the methanol/HCl complex formed in the alachlor process described in the above Example, the methanol/HCl comlex from the separation stage(s) is fed to a steam distillation system from which purified methanol is obtained.

With further respect to the present process, while the use of technical grade reactants, i.e., the compounds of Formulae II and III, is suitable, it will be appreciated that the higher the purity of these reactants, the higher the quality of compounds of Formula I will be produced. Although in some instances the Formula III compounds, e.g., methanol, containing minor amounts of water can be used, it is much more preferable to use anhydrous compounds, because water may cause hydrolysis of the Formula II reactants resulting in deteriorated product of Formula I. However, it will be understood that in special case where $R_1$ may be hydrogen, water itself can be used as the compound of Formula III to produce some compounds of Formula I by hydrolysis of the N-haloalkyl intermediate. For example, it has been disclosed in the prior art that 2'-tert-butyl-6'-ethyl-N-(chloromethyl)-2-chloroacetanilide is hydrolyzed with water in the presence of an acid binding agent to produce the corresponding N-hydroxymethyl compound which is useful as a herbicide (see, e.g., Example 1 in British Patent No. 1,088,397). Accordingly, it will be appreciated that in some embodiments of the present process the presence of some water may be detrimental to product yield but not in other embodiments, depending upon the reactivity of water with other reactants and final products as will be understood by those skilled in the art. In like manner, since hydrogen halide adversely impacts on product quality, it is preferred to use reactants substantially free of hydrogen halides such as HCl.

Representative compounds produced according to the process of this invention include those in which the groups of the above formulae have the following identities:

R is $C_{1-5}$ haloalkyl, preferably $C_{1-2}$ monohaloalkyls, such as chloromethyl, chloroethyl, bromomethyl, bromoethyl, iodomethyl, iodoethyl, fluoromethyl and fluoroethyl; dihaloalkyls such as 1,1-dichloromethyl, 1,1-dibfomomethyl, 1,1-diodomethyl, etc., may also be present.

$R_1$-hydrogen, $C_{1-10}$ alkyls, e.g., methyl, ethyl, propyls, butyls, pentyls, hexyls, heptyls, octyls, nonyls, decyls, etc., $C_{1-10}$ alkenyls, e.g., vinyl, allyl, crotyl, methallyl, butenyls, pentyls, hexenyls, heptenyls, octenyls, nonenyls, decenyls; $C_{1-10}$ alkynyls, e.g., ethynyl, propynyls, butynyls, pentynyls, hexynyls, etc.; the alkoxy, polyalkoxy, alkoxyalkyl and polyalkoxyalkyl analogs of the foregoing alkyl groups; cycloalkyls and alkylcycloalkyls having up to 7 cyclic carbons, e.g., cyclopropyl, cyclobutyl, cyclopentyl, cyclohexyl, cycloheptyl, cyclopropylmethyl, cyclobutylmethyl, cyclopentylmethyl, etc.; cycloalkenyls and cycloalkadienyls having up to 7 cyclic carbons, e.g., cyclopentenes, cyclohexenes and cycloheptenes having mono- and di-unsaturation; $C_{6-12}$ aryl and aralkyl and alkaryl groups, e.g., phenyl, tolyls, xylyls, benzyl, naphthyl, etc., amino and mono- and di-substituted amino containing $C_{1-6}$ alkyl, alkenyl or alkynyl groups; sulfinyl, sulfonyl and sulfonate groups which may be substituted by $C_{1-6}$ alkyl, alkenyl, amino or substituted amino groups and the above $R_1$ members which may be substituted with substituents such as alkyl, halogen, hydroxy, alkoxy, nitro, cyano or alkylthio.

$R_2$ and $R_3$-hydrogen, chlorine, bromine, iodine, fluorine, $C_{1-6}$ alkyl, haloalkyl, e.g., chloromethyl, chloroethyl, bromomethyl, bromoethyl, iodomethyl, iodoethyl, trifluoromethyl, chloropropyl, bromopropyl, iodopropyl, chlorobutyl, iodobutyl and di- and trihalo analogs thereof; alkoxys, e.g., methoxy, ethoxy, propoxys, butoxys, pentoxys and hexoxys and corresponding polyalkoxys and alkoxyalkyls, e.g., methoxymethoxy, methoxyethoxy, ethoxymethoxy, ethoxyethoxy, methoxymethyl, methoxyethyl, ethoxymethyl, ethoxyethyl, propoxymethyl, isopropoxymethyl, butoxymethyl, isobutoxymethyl, tertbutoxymethyl, pentoxymethyl, hexoxymethyl, etc.

$R_4$ may be hydrogen, the halo, alkyl, haloalkyl, alkoxy and alkoxyalkyl groups of $R_1$, $R_2$ and $R_3$, methylthio, ethylthio, propylthio, CN, $NO_2$, $CF_3$ or $R_4$ may be combined with $R_2$ or $R_3$ to form an alkylene chain of up to 4 carbon atoms, thus forming acylated 5-aminotetralins and acylated 4-aminoindanes typified in the above-mentioned U.S. Pat. No. 3,875,228.

X is halo, especially chlorine or bromine.

The process of the present invention is particularly amenable to use in the preparation of the above N-substituted-2-haloacetanilides wherein $R_1$, $R_2$ and $R_3$ are $C_{1-6}$ alkyl, R is monohalomethyl and Y is oxygen.

Compounds of Formula I prepared according to this invention are known compounds. Representative compounds of Formula I are disclosed in the prior art described in the foregoing section entitled "Description of the Prior Art" and other prior art not cited herein.

It will be appreciated by those skilled in this art that the preferred 2-haloacetanilides are a subgenus of N,N-di-substituted-2-haloacylamides. Accordingly, the process of this invention may be modified in a manner within the skill of this art as the nature and concentration of reactants, reaction and separation conditions of temperature, pressure, residence times, etc., to produce other compounds within a broad genesis of said N,N-disubstituted-2-haloacylamides.

We claim:

1. Process for the preparation of compounds of Formula I

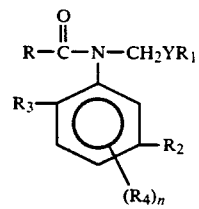

wherein

R is $C_{1-5}$ haloalkyl;

Y is oxygen or sulfur;

$R_2$ is $C_{1-10}$ alkyl, alkenyl, alkynyl, alkoxyalkyl, $C_{3-7}$ cycloalkyl, lower alkylcycloalkyl or cycloalkenyl, $C_{6-12}$ aryl or aralkyl, or said $R_1$ members substituted with $C_{1-4}$ lower alkylthio, halogen, hydroxy, nitro or cyano;

$R_2$, $R_3$ and $R_4$ are independently hydrogen, halogen, $C_{1-6}$ alkyl, haloalkyl, alkoxy or alkoxyalkyl, n is an integer from 0–3 inclusive, which comprises performing at least one sequence of reaction/separation operations comprising:

(A) reacting a compound of Formula II

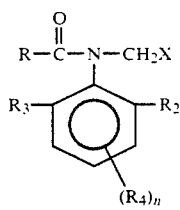

with a compound of Formula III $$R_1YH \quad \quad (III)$$

wherein R, R$_1$-R$_4$, Y, and n are as defined above and X is halogen, in the absence of an acid-binding agent for period of time required to reach equilibrium and thereafter without delay, (B) directing an effluent stream of the reaction mixture from Step (A) to a separation zone wherein means are employed to rapidly remove a gaseous mixture containing a complex of by-product HX with said compound of Formula III from a liquid product stream comprising predominantly said compound of Formula I.

2. Process according to claim 1 in which said reaction/separation process is carried out in a sequence of two stages which comprises:

Performing the (A) and (B) reaction/separation operations as described in claim 1;

(C) directing said product stream from said first separation zone to a second reaction zone into which is also introduced an additional quantity of said compound of Formula III to react with said unreacted compound of Formula II in the absence of an acid-binding agent for a period of time required to reach equilibrium and thereafter without delay;

(D) directing an effluent stream of the reaction mixture of Step (C) to a second separation zone wherein means are employed to rapidly remove a gaseous mixture containing substantially all of the remaining by-product HX as a complex with said compound of Formula III and a liquid product stream comprised of said compound of Formula I and tract impurities.

3. Process according to claim 1 wherein said reaction/separation process sequence is repeated a plurality of times to assure complete conversion of said compound of Formula II to said compound of Formula I.

4. Process according to claim 2 wherein Step (A) is conducted at a temperature within the range of from about −25° to 125° C.

5. Process according to claim 2 wherein Step (C) is conducted at temperatures within the range of from about −25° to 175° C.

6. Process according to claim 2 wherein the compound of Formula III is used in an amount corresponding to a molar ratio of >1:1 relative to the compound of Formula II.

7. Process according to claim 6 wherein said molar ratio is within the range of about 2-100:1.

8. Process according to claim 2 wherein said complex of HX with compound of Formula III from Step (D) is fed to a recovery system from which said compound of Formula III is removed from said hydrogen halide, purified and recycled to Steps (A) and/or (C).

9. Process according to claim 1 wherein temperatures in Steps (B) and (D) are within the range of about 50° C. to 175° C. and pressures are within the range of about 1.0 to 300 mm Hg absolute.

10. Process according to claim 1, wherein in said formulae

X is chlorine;
Y is oxygen;
R is monohalomethyl,
R$_1$ is C$_{1-6}$ alkyl;
R$_2$, R$_3$ and R$_4$ are independently hydrogen, halogen, C$_{1-6}$ alkyl, haloalkyl, alkoxy or alkoxyalkyl, and
n is an integer of 0-2, inclusive.

11. Process according to claim 10 wherein in Formula I
R$_1$, R$_2$ and R$_3$ are C$_{1-6}$ alkyl;
R is monochloromethyl; and
n is zero.

12. Process according to claim 11 wherein
R$_1$ is methyl, ethyl, propyl or butyl, and
R$_2$ and R$_3$ are methyl or ethyl.

13. Process according to any of claims 1, 2, 3, 4, 5, 6, 11 or 12 wherein said compound of Formula III is ethanol.

14. Process for preparation and recovery of alachlor or butachlor which comprises performing at least one sequence of reaction/separation operations comprising:

(A) reacting methanol or butanol with 2′,6′-diethyl-N-(chloromethyl)-2-chloroacetanilide at a molar ratio of about 2-100:1 at temperatures within the range of from about 25°-65° for a period of time required to reach equilibrium within about 15-30 minutes in the absence of added acid binders, and thereafter without delay;

(B) directing an effluent stream of the reaction mixture from Step (A) to a separation zone wherein means are employed to rapidly remove a gaseous mixture containing a complex of HCl and methanol or butanol and a liquid product stream comprising predominantly alachlor or butachlor.

15. Process according to claim 14 wherein said reaction/separation sequence is repeated a plurality of times to assure substantially complete conversion of 2′,6′-diethyl-N-(chloromethyl)-2-chloroacetanilide to alachlor or butachlor.

16. Process according to claim 15 which comprises:

(A) reacting in a first reaction zone maintained at about 25°-65° C. methanol or butanol with 2′,6′-diethyl-N-(chloromethyl)-2-chloroacetanilide at a molar feed ratio of about 2-10:1 in the absence of added acid binders for a period of time required to reach equilibrium within about 15 to 30 minutes, and therafter without delay;

(B) directing an effluent stream of the reaction mixture of Step (A) to a flash distillation zone maintained at temperatures and pressures within the ranges of about 50°-100° C. and 30-300 mm Hg absolute from which is removed a gaseous mixture containing a complex of methanol or butanol and most of by-product HCl and a liquid product stream comprising predominantly alachlor or butachlor and unreacted 2′,6′-diethyl-N-(chloromethyl)-2-chloroacetanilide.

(C) directing said product stream from said first separation zone to a second reaction zone maintained at about 25°-65° C. into which is also introduced an additional quantity of methanol or butanol to react with said unreacted 2′,6′-diethyl-N-(chloromethyl)-2-chloroacetanilide in an amount corresponding to the amount used in first reaction zone in the absence of acid binders for a period of time required to reach equilibrium within about 15 to 30 minutes and thereafter without delay;

(D) directing an effluent stream of the reaction mixture of Step (C) to a second flash distillation zone maintained at temperatures and pressures within the ranges of about 50°–100° C. and 30–300 mm Hg absolute from which is removed a gaseous mixture containing a complex comprising methanol or butanol and substantially all of the remaining by-product HCl and a liquid product stream comprised of alachlor or butachlor and trace impurities.

17. Process according to claim 16 wherein said complex of methanol or butanol and HCl from Steps (B) and (D) are combined and fed to a methanol or butanol recovery system from which HCl is removed and recovered methanol or butanol is purified and recycled to Steps (A) and/or (C).

18. Process according to claim 17 wherein the residence time of said reaction mixture in said flash distillation zones of Steps (B) and (D) is <0.5 minute.

* * * * *

UNITED STATES PATENT AND TRADEMARK OFFICE
CERTIFICATE OF CORRECTION

PATENT NO. : 5,155,272
DATED : 10/13/92
INVENTOR(S) : Donald E. Baldus, Edward E. Debus It is certified that error appears in the above-identified patent and that said Letters Patent is hereby corrected as shown below:

Col. 4, lines 10-18, and Col. 14, lines 44-53, amend Formula I to read:

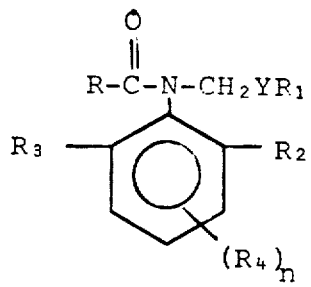

Col. 5, line 1, "2',640" should be -- 2',6' --.

Col. 9, line 28 "n26D26" should read -- $n_D^{26}$ --.

Col. 10, line 42 "2',4',640" should be -- 2',4',6'- --.

Col. 12, line 66 "comlex" should be -- complex --.

Col. 13, line 39, "dibfomomethyl" should be -- dibromomethyl --.

UNITED STATES PATENT AND TRADEMARK OFFICE
CERTIFICATE OF CORRECTION

PATENT NO. : 5,155,272
DATED : October 13, 1992
INVENTOR(S) : Donald E. Baldus, Edward E. Debus It is certified that error appears in the above-indentified patent and that said Letters Patent is hereby corrected as shown below:

Col. 15, Line 15, "$R_1$" should be --$R_2$--.

Signed and Sealed this

Twenty-eighth Day of December, 1993

Attest:

BRUCE LEHMAN

*Attesting Officer*        *Commissioner of Patents and Trademarks*